(12) United States Patent
Utsumi et al.

(10) Patent No.: US 10,139,409 B2
(45) Date of Patent: Nov. 27, 2018

(54) **METHOD FOR DETECTING *STREPTOCOCCUS* BACTERIUM CONTAINED IN MILK**

(71) Applicant: ASAHI KASEI KABUSHIKI KAISHA, Tokyo (JP)

(72) Inventors: Takamitsu Utsumi, Tokyo (JP); Koji Maehana, Tokyo (JP); Kenji Matsuyama, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/105,481

(22) PCT Filed: Dec. 17, 2014

(86) PCT No.: PCT/JP2014/083461
§ 371 (c)(1),
(2) Date: Jun. 16, 2016

(87) PCT Pub. No.: WO2015/093546
PCT Pub. Date: Jun. 25, 2015

(65) Prior Publication Data
US 2016/0313328 A1 Oct. 27, 2016

(30) Foreign Application Priority Data
Dec. 18, 2013 (JP) .................... 2013-261825

(51) Int. Cl.
| | | |
|---|---|---|
| *C12N 1/06* | (2006.01) | |
| *G01N 33/569* | (2006.01) | |
| *C12Q 1/14* | (2006.01) | |
| *C12N 9/24* | (2006.01) | |
| *B01D 15/12* | (2006.01) | |
| *B01D 15/38* | (2006.01) | |
| *C12N 9/36* | (2006.01) | |

(52) U.S. Cl.
CPC ....... *G01N 33/56944* (2013.01); *B01D 15/12* (2013.01); *B01D 15/3809* (2013.01); *C12N 1/06* (2013.01); *C12N 9/2402* (2013.01); *C12N 9/2462* (2013.01); *C12Q 1/14* (2013.01); *C12Y 302/01017* (2013.01); *C12Y 302/01096* (2013.01); *G01N 2333/315* (2013.01)

(58) Field of Classification Search
None
See application file for complete search history.

(56) References Cited

U.S. PATENT DOCUMENTS

| | | |
|---|---|---|
| 9,339,533 B2 | 5/2016 | Beck et al. |
| 2004/0258664 A1 | 12/2004 | Pitcovski et al. |
| 2010/0272759 A1 | 10/2010 | Beck et al. |
| 2011/0020861 A1 | 1/2011 | Colin et al. |
| 2012/0329050 A1 | 12/2012 | Nadeau et al. |

FOREIGN PATENT DOCUMENTS

| | | |
|---|---|---|
| JP | 01-244370 | 9/1989 |
| JP | 3-501653 A | 4/1991 |
| JP | 09-227392 | 9/1997 |
| JP | 2003-171291 | 6/2003 |
| JP | 2006-504619 A | 2/2006 |
| JP | 2011-512861 A | 4/2011 |
| JP | 2012-122921 A | 6/2012 |
| JP | 2012-524548 | 10/2012 |
| WO | WO 90/10232 A1 | 9/1990 |
| WO | WO 03/076471 A2 | 9/2003 |
| WO | WO 2003/076471 A3 | 9/2003 |
| WO | WO 2007/013452 A1 | 2/2007 |
| WO | WO 2010/124154 A1 | 10/2010 |

OTHER PUBLICATIONS

Garcia et al., "Purification and Characterization of the Autolytic Glycosidase of *Streptococcus pneumoniae*", Biochemical and Biophysical Research Commuications, vol. 158, No. 1 (1989) pp. 251-256.

International Preliminary Report on Patentability issued in International Application No. PCT/JP2014/083461 dated Jun. 30, 2016.

International Search Report issued in International Application No. PCT/JP2014/083461 dated Mar. 31, 2015.

Kitchen et al., "Relationship Between the Level of N-Acetyl-β-D-glucosaminidase NAGase) in Bovine Milk and the Presence of Mastitis Pathogens", Journal of Dairy Research, vol. 51 (1954) pp. 11-16.

Niwa et al., Lytic Enzyme, Labiase for a Broad Range of Gram-positive Bacteria and its Application to Analyze Functional DNA/RNA, Journal of Microbiologial Methods, vol. 61 (2005) pp. 251-260.

Oana et al., "Simple Broad-Spectrum Protocol Using Labiase for Bacterial Cell Lysis to Prepare Genomic DNA for Pulsed-Field Gel Electrophoresis Analysis", Microbiol Immunol, vol. 53 (2009) pp. 45-48.

Gillespie et al., "Simultaneous Detection of Mastitis Pathogens, *Staphylococcus aureus*, *Streptococcus uberis*, and *Streptococcus agalactiae* by Multiplex Real-Time Polymerase Chain Reaction," Journal of Dairy Science, vol. 88, No. 10, Oct. 1, 2005, pp. 3510-3518.

(Continued)

*Primary Examiner* — Jennifer E Graser
(74) *Attorney, Agent, or Firm* — Birch, Stewart, Kolasch & Birch, LLP (57) ABSTRACT

The object is to provide a lysis method and lysis treatment solution for efficiently lysing cells of various *Streptococcus* bacteria in milk of a livestock animal to release a specific antigen substance contained in the cells for detecting whether causative bacterium of mastitis is a *Streptococcus* bacterium or not by using the milk, as well as a detection method using an immunochromatographic device. There is provided a method for lysing a *Streptococcus* bacterium, which comprises the step of mixing a lysis agent containing a lytic enzyme with milk obtained form a livestock animal to lyse a *Streptococcus* bacterium existing in the milk. The lytic enzyme is preferably at least one selected from the group consisting of lysozyme, labiase, and β-N-acetylglucosaminidase.

5 Claims, 1 Drawing Sheet

(56) References Cited

OTHER PUBLICATIONS

Ongol et al., "A real-time PCR method targeting a gene sequence encoding 16S rRNA processing protein, rimM, for detection and enumeration of *Streptococcus thermophilus* in dairy products," Food Research International, vol. 42, No. 8, Oct. 1, 2009, pp. 893-698.
Partial Supplementary European Search Report issued in European Application No. 14872507.0, dated Jun. 2, 2017.
Sentitula et al., "Incidence of *Staphylococci* and *Streptococci* During Winter in Mastitic Milk of Sahiwal Cow and Murrah Buffaloes," Indian Journal of Microbiology, vol. 52, No. 2, Apr.-Jun. 2012 (published online Aug. 9, 2011), pp. 153-159.
Extended European Search Report, dated Oct. 11, 2017, for corresponding European Application No. 14872507.0.
Pang et al., "Selection of surfactants for cell lysis in chemical cytometry to study protein-DNA interactions," Electrophoresis, vol. 27, 2006, pp. 1489-1494.

METHOD FOR DETECTING STREPTOCOCCUS BACTERIUM CONTAINED IN MILK

TECHNICAL FIELD

The present invention relates to a lysis method and detection method for detecting a *Streptococcus* bacterium, which is a causative bacterium of mastitis, in milk of livestock.

BACKGROUND ART

Milk of livestock animals, of which typical examples are cow, sheep, and goat, may not be sterile, and may be contaminated with certain microorganisms due to diseases or environment. In particular, it is known that animals with a disease caused by infection of a microorganism in the udder often discharge a lot of the microorganisms into milk. Typical diseases of livestock animals caused by infection of a microorganism include mastitis.

Mastitis is inflammation of the laticifer system or milk gland tissue, and it is caused largely by invasion, colonization and proliferation of a microorganism in the udder. Although many kinds of animals contract mastitis, it is said that, especially concerning cow's mastitis in dairy cows, 15 to 40% of the whole dairy cows contract mastitis, and thus it is one of the extremely important diseases for dairy farmers. If a dairy cow contracts mastitis, not only the milk synthesis function is inhibited to result in reduction of lactation amount, or even stop of lactation as the case may be, but also enormous economical losses are imposed on dairy farmers, such as cost of medical treatment and penalty concerning milk price due to degradation of milk quality. Furthermore, it also increases the labor of dairy farmers, since, for example, milking of teats suffering from mastitis must be separately performed for preventing infection.

Mastitis is caused by infection of various microorganisms. Among the causative bacteria, *Streptococcus* bacteria (also referred to as streptococci) are known as frequently found causative bacteria.

As the method for detecting *Streptococcus* bacteria in milk, cultivation-based methods are widely used. Since the cultivation-based methods require several days for obtaining a result, they are not suitable for quick identification of causative bacteria. In contrast, identification methods based on an antigen-antibody reaction using an antibody directed to an ingredient specific to a causative bacterium, especially the immunochromatographic method, can provide the result in several tens of minutes, and therefore they are widely used as quick and convenient inspection methods (for example, Patent document 1). The inventors of the present invention have examined use of an immunochromatographic method also as a method for detecting a substance contained in milk of livestock animals (Patent document 2).

In immunological measurement methods such as the immunochromatographic method, when an antigen as target of the detection is an ingredient contained in bacterial cells, it is necessary to lyse bacterial cells to release antigens from the inside of the cells to the outside of the cells. It is known that labiase exhibits bacteriolytic activity against *Streptococcus* bacteria (Non-patent document 1). However, Non-patent document 1 does not describe lysis effect in a high protein and high fat content solution such as milk.

PRIOR ART REFERENCES

Patent Documents

Patent document 1: Japanese Patent Unexamined Publication (KOKAI) No. 1-244370
Patent document 2: Japanese Patent Unexamined Publication (KOKAI) No. 2012-122921

Non-Patent Document

Non-patent document 1: Microbiol. Immunol., 2009, 53:45-48

SUMMARY OF THE INVENTION

Object to be Achieved by the Invention

Mastitis is caused by infection of various microorganisms, and therefore antibiotics that exhibit efficacy in therapeutic treatment therefor may differ depending on type of causative microorganism. Therefore, early diagnosis and therapeutic treatment of mastitis are very important. Further, when certain specific types of microorganisms have caused mastitis, they may transmit to other teats of the individual or other individuals, and therefore it is extremely important to quickly and conveniently identify the causative bacteria existing in milk.

The cultivation-based methods widely used as methods for detecting a bacterium have a problem that they require several days to obtain a result. In contrast, the immunological measurement methods based on an antigen-antibody reaction, such as the immunochromatographic method, have an advantage that they enable quick and convenient detection of causative bacteria, and thus enable early therapeutic treatment with an antibacterial agent. In order to highly sensitively detect a specific substance in cells of a causative bacterium by an immunological measurement method, when the specific substance (antigen) is an intracellular ingredient, it is necessary to highly efficiently lyse the cells to release the antigen in the inside of the cells to the outside of the cells. However, when milk is used as a test sample, conventional techniques cannot provide sufficient lysis in many cases, because of the influences of proteins such as casein, milk fat globules, and so forth contained in milk in large amounts. According to the investigations of the inventors of the present invention, it has been found that activities of common lytic enzymes markedly reduce in a system containing milk. As described above, any effective lysis method for detecting a *Streptococcus* bacterium contained in milk is not known among the conventional techniques.

An object of the present invention is to provide a lysis method and lysis treatment solution for efficiently lysing various *Streptococcus* bacteria in milk of a livestock animal to release a specific antigen substance contained in cells for detecting whether causative bacterium of mastitis is a *Streptococcus* bacterium or not by using the milk, as well as a detection method using an immunochromatographic device.

Means for Achieving the Object

The inventors of the present invention found that *Streptococcus uberis* contained in milk can be efficiently lysed by using a lysis agent containing at least lysozyme or labiase, and *Streptococcus agalactiae* can be efficiently lysed by using a lysis agent containing a lytic enzyme selected from lysozyme, labiase, and β-N-acetylglucosaminidase. They further found that, for efficiently performing a lysis treatment of *Streptococcus* bacteria contained in milk, the cells can be highly efficiently lysed by using the labiase enzyme known to have a lysis activity together with lysozyme further added in a specific amount, so that the L7/L12 protein contained in the cells can be released, and such lysis can be used for highly sensitive detection of *Streptococcus* bacteria, and accomplished the present invention.

The present invention thus provides the followings.

[1] A method for lysing a *Streptococcus* bacterium, which comprises:

the step of mixing a lysis agent containing at least one selected from the group consisting of lysozyme, labiase, and β-N-acetylglucosaminidase with milk obtained form a livestock animal to lyse a *Streptococcus* bacterium existing in the milk, and wherein:

the *Streptococcus* bacterium is *Streptococcus uberis*, and the lysis agent contains at least one of lysozyme and labiase, or the *Streptococcus* bacterium is *Streptococcus agalactiae*, and the lysis agent contains at least one selected from the group consisting of lysozyme, labiase, and β-N-acetylglucosaminidase.

[2] A method for lysing a *Streptococcus* bacterium, which comprises the step of mixing a lysis agent containing at least lysozyme and labiase with milk obtained form a livestock animal to lyse the bacterium existing in the milk.

[3] A lysis agent for lysing a *Streptococcus* bacterium contained in milk, which contains at least one selected from the group consisting of lysozyme, labiase, and β-N-acetylglucosaminidase, or contains at least lysozyme and labiase.

[4] The lysis agent according to [3], which is for use in a method for diagnosing mastitis of a livestock animal.

[5] A method for detecting a *Streptococcus* bacterium contained in milk of a livestock animal, which comprises the method according to [1] or [2], and further comprises the step of detecting a specific substance derived from the inside of cells and released by lysis.

[6] The method according to [5], wherein the step of detecting a specific substance is performed by an immunochromatographic method.

The present invention also provides the followings.

[1] A method for lysing a *Streptococcus* bacterium contained in milk, which comprises the step of mixing a lysis agent containing lysozyme, labiase, and a nonionic surfactant with the milk to lyse the bacterium existing in the milk, or the step of mixing a lysis agent containing at least one selected from the group consisting of lysozyme, labiase, and β-N-acetylglucosaminidase with the milk to lyse the bacterium existing in the milk, wherein the *Streptococcus* bacterium is *Streptococcus agalactiae*.

[2] The lysis method according to [1], wherein the bacterium is *Streptococcus uberis* or *Streptococcus agalactiae*.

[3] The lysis method according to [1] or [2], wherein the nonionic surfactant comprises a polyoxyethylene alkyl phenyl ether and/or a polyoxyethylene sorbitan fatty acid ester.

[4] The lysis method according to any one of [1] to [3], wherein, in the step of mixing the lysis agent with the milk to lyse the bacterium existing in the milk, final concentration of the nonionic surfactant is not lower than 0.03% and not higher than 3%.

[5] The lysis method according to [4], wherein, in the step of mixing the lysis agent with the milk to lyse the bacterium existing in the milk, final concentration of lysozyme is not lower than 0.5 mg/ml and not higher than 200 mg/ml; and/or in the step of mixing the lysis agent with the milk to lyse the bacterium existing in the milk, final concentration of labiase is not lower than 0.05 mg/ml and not higher than 20 mg/ml.

[6] A method for detecting a *Streptococcus* bacterium contained in milk, which comprises:

the step of mixing the lysis agent with the milk to lyse the bacterium existing in the milk defined in any one of [1] to [5], and further comprises:

the step of detecting a specific substance derived from the inside of the bacterium cell and released by lysis.

[7] The detection method according to [6], which is performed by an immunochromatographic method.

[8] The detection method according to [7], wherein the immunochromatographic method comprises (1) the step of contacting the milk containing the specific substance with a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk, at the third part or a part existing upstream therefrom, and (2) the step of flowing the milk up to the second part or a part existing downstream therefrom to obtain a detectable signal of the label at the second part or a part existing downstream therefrom.

[9] The detection method according to [8], wherein the labeled first antibody directed to the specific substance is retained in the first part.

[10] The detection method according to [8] or [9], wherein the third part is constituted by two or more kinds of members having voids that can remove milk fat globules of different particle sizes, respectively.

[11] The detection method according to [10], wherein the third part is constituted by a first member disposed downstream and a second member disposed upstream, and retention particle size of the second member is larger than retention particle size of the first member.

[12] The lysis agent defined in any one of [1] to [5].

[13] The lysis agent according to [12], which is for use in a method of diagnosing mastitis of a livestock animal.

[14] A kit for detecting a *Streptococcus* bacterium contained in milk, which comprises:

the lysis agent according to [12] or [13], and an immunochromatographic device for detecting a specific substance contained in milk, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk.

Effect of the Invention

It was found that, as for lysis of *Streptococcus uberis* or *Streptococcus agalactiae*, they can be highly efficiently lysed by using a specific lytic enzyme for each bacterial species, and as for lysis of *Streptococcus* bacteria, they can be highly efficiently lysed by using labiase and a specific amount of lysozyme in combination as lytic enzymes.

MODES FOR CARRYING OUT THE INVENTION

Hereafter, the present invention will be explained in more detail. In the present invention, when a numerical value range is represented as "X to Y", the range includes the values X and Y as the minimum and maximum values. The symbol "%" is used for indicating percent on mass basis, unless especially indicated. The expression "A and/or B" means at least one of A and B, including the cases of referring to only A, only B, and A and B.

The present invention provides a lysis agent for lysing Streptococcus bacteria contained in milk. The lysis agent of the present invention contains a lytic enzyme.

[Lytic Enzyme]

Type of the lytic enzyme used in the present invention is not particularly limited, and arbitrary two or more kinds of lytic enzymes may also be used in combination, as required. In the present invention, it is preferable to use at least one selected from the group consisting of lysozyme, labiase, and β-N-acetylglucosaminidase. When the Streptococcus bacterium is Streptococcus uberis, the lysis agent preferably contains at least one of lysozyme and labiase, and when the Streptococcus bacterium is Streptococcus agalactiae, the lysis agent preferably contains at least one selected from the group consisting of lysozyme, labiase, and β-N-acetylglucosaminidase.

Labiase is prepared from culture supernatant of the Streptomyces fulvissimus TU-6 strain, and is a complex enzyme mainly consisting of β-N-acetyl-D-glucosaminidase and muramidase. Labiase can be prepared from culture supernatant of the aforementioned strain, or can also be obtained by purchasing a marketed product.

When labiase is used, especially when that described in the examples mentioned in this specification is used, from the viewpoint of efficiently performing lysis, final concentration thereof can be preferably 0.05 mg/ml or higher, more preferably 0.1 mg/ml or higher, still more preferably 0.5 mg/ml or higher, and in any case, it can be 20 mg/ml or lower, preferably 10 mg/ml or lower, more preferably 5 mg/ml or lower. Alternatively, the final concentration thereof can be 0.0005 unit/ml or higher, preferably 0.001 unit/ml or higher, more preferably 0.005 unit/ml or higher, and in any case, it can be 0.2 unit/ml or lower, preferably 0.1 unit/ml or lower, more preferably 0.05 unit/ml or lower. When the term enzyme unit (unit) is mentioned for labiase in this specification, it refers to a value of the β-N-acetyl-D-glucosaminidase activity, and the enzymatic activity that releases 1 μmol of p-nitrophenol in 1 minute when the enzyme is allowed to act on p-nitrophenyl-β-N-acetyl-D-glucosamine as a substrate is defined as 1 unit, unless especially indicated.

Lysozyme is a protein consisting of a single peptide of 14.6 kDa, and can lyse cells of bacteria by cleaving the β(1-4) glycosidic linkage between N-acetylmuramic acid and N-acetylglucosamine in the peptidoglycan layer. Lysozyme can be obtained by purchasing a marketed product.

When lysozyme is used, especially when that described in the examples mentioned in this specification is used, from the viewpoint of efficiently performing lysis, final concentration thereof can be preferably 0.5 mg/ml or higher, more preferably 1 mg/ml or higher, still more preferably 5 mg/ml or higher, and in any case, it can be 200 mg/ml or lower, preferably 100 mg/ml or lower, more preferably 50 mg/ml or lower. Alternatively, the final concentration of lysozyme can be preferably 0.4 mg/ml or higher, more preferably 0.8 mg/ml or higher, still more preferably 4 mg/ml or higher, and in any case, it can be 160 mg/ml or lower, preferably 80 mg/ml or lower, more preferably 40 mg/ml or lower. When amount as lysozyme is referred to in this specification for lysozyme, it is a value determined on the basis of decrease of absorbance (640 nm) observed when it is allowed to act on a suspension of dry cells of Micrococcus Lysodeikticus in a phosphate buffer as a substrate, unless especially indicated.

β-N-Acetylglucosaminidase is also called β-N-acetylhexosaminidase, and is an enzyme that releases terminal β-linked N-acetylglucosamine and N-acetylgalactosamine from various substrates. β-N-Acetylglucosaminidase can be obtained by purchasing a marketed product.

When β-N-acetylglucosaminidase is used, especially when that described in the examples mentioned in this specification is used, from the viewpoint of efficiently performing lysis, final concentration thereof can be preferably 0.5 mg/ml or higher, more preferably 1 mg/ml or higher, still more preferably 5 mg/ml or higher, and in any case, it can be 200 mg/ml or lower, preferably 100 mg/ml or lower, more preferably 50 mg/ml or lower. Alternatively, the final concentration thereof can be preferably 0.05 unit/ml or higher, more preferably 0.1 unit/ml or higher, still more preferably 0.5 unit/ml or higher, and in any case, it can be 200 units/ml or lower, preferably 100 units/ml or lower, more preferably 50 unit/ml or lower. When the term enzyme unit (unit) is mentioned for β-N-acetylglucosaminidase in this specification, the enzymatic activity that releases 1 μmol of p-nitrophenol in 1 minute when the enzyme is allowed to act on p-nitrophenyl-β-N-acetyl-D-glucosamine as a substrate is defined as 1 unit, unless especially indicated.

According to the present invention, by further supplementarily adding the enzyme lysozyme to milk containing Streptococcus bacteria in addition to the enzyme labiase, highly efficient lysis effect can be attained, which effect can be applied to a wide range of Streptococcus bacteria. When the lysozyme and labiase described in the section of examples of this specification are used, from the viewpoint of efficiently performing lysis, amount of lysozyme to be supplementarily added is preferably 3 mg/ml or larger, more preferably 5 mg/ml or larger, further preferably 7 mg/ml or larger, still further preferably 9 mg/ml or larger, and preferably 100 mg/ml or smaller, more preferably 50 mg/ml or smaller, further preferably 20 mg/ml or smaller, per 1 mg/ml of labiase. Alternatively, amount of lysozyme to be supplementarily added is preferably 2.4 mg/ml or larger, more preferably 4 mg/ml or larger, further preferably 5.6 mg/ml or larger, still further preferably 7.2 mg/ml or larger, and in any case, preferably 80 mg/ml or smaller, more preferably 40 mg/ml or smaller, further preferably 16 mg/ml or smaller, per 0.1 unit/ml of labiase.

[Surfactant]

A surfactant that ionizes and becomes an ion, when it is dissolved in water, is referred to as ionic surfactant, and a surfactant that does not become an ion is referred to as non-ionic (nonionic) surfactant. Ionic surfactant is further classified into anionic surfactant, cationic surfactant, and ampholytic surfactant.

It can be expected that, by adding a surfactant to the lysis agent in addition to the lytic enzyme, the lysis effect thereof can be enhanced. As the surfactant, any of nonionic surfactant, cationic surfactant, anionic surfactant, and ampholytic surfactant can be independently used, or any of these may be used in combination.

The lysis agent of the present invention can contain a nonionic surfactant. It is considered that coexistence of a nonionic surfactant is particularly preferred, when the obtained cell lysate is used in an immunochromatographic method. It is considered that, as the nonionic surfactant, any of those of ester ether type, ester type, and ether type can be preferably used. More specifically, examples include polyoxyethylene alkyl ethers, polyoxyethylene alkyl phenyl ethers, fatty acid sorbitan esters, alkyl polyglucosides, fatty acid diethanolamides, alkyl monoglyceryl ethers, polysorbates (formed by condensation of several tens of molecules of ethylene oxide to a fatty acid sorbitan ester), and so forth, but it is not particularly limited. Especially preferred examples include polysorbates, more specifically, polyoxyethylene (20) sorbitan monolaurate, polyoxyethylene (60) sorbitan monostearate, polyoxyethylene (65) sorbitan tristearate, and polyoxyethylene (80) sorbitan monooleate, and so forth, as well as polyoxyethylene alkyl phenyl ethers, more specifically, polyoxyethylene (10) octyl phenyl ether, and so forth.

Content of the nonionic surfactant in the lysis agent (when two or more kinds of nonionic surfactants are used, it is the content as the total amount of the nonionic surfactants) is not particularly limited so long as, for example, when an immunochromatographic method is used, flow of a developing solution is secured. However, in any case, as for the lower limit thereof, the content can be determined so that the final concentration of the nonionic surfactant in the mixture with milk becomes 0.03% or higher, preferably 0.05% or higher, more preferably 0.075% or higher, further preferably 0.1% or higher, particularly preferably 0.3% or higher. As for the upper limit of the content of the nonionic surfactant, the content can be determined so that the reaction catalyzed by the lytic enzyme and antigen-antibody reactions are not significantly inhibited, and in any case, it can be 10% or lower, preferably 7.5% or lower, more preferably 5.0% or lower, still more preferably 3% or lower, particularly preferably 2% or lower.

As the anionic surfactant, any of carboxylic acid salts, sulfonic acid salts, sulfuric acid ester salts, and so forth can be preferably used. More specific examples include alkyl ether carboxylates, linear alkylbenzenesulfonates (LAS), α-olefinsulfonates (AOS), dialkylsulfosuccinates, formaldehyde condensates of naphthalenesulfonate, alkylsulfuric acid ester salts (AS), polyoxyethylenealkylsulfuric acid ester salts (AES) obtained by addition of ethylene oxide to a higher alcohol and following sulfation, phosphoric acid ester salts of a higher alcohol or ethylene oxide adduct thereof, and so forth. Further specific examples include sodium alkylsulfates such as sodium dodecylsulfate and sodium myristylsulfate, sodium N-acylsarcosinates such as sodium N-lauroylsarcosinate and sodium N-myristoylsarcosinate, sodium dodecylbenzenesulfonate, hydrogenated coconut fatty acid monoglyceride monosodium sulfate, sodium laurylsulfoacetate, N-acylglutamates such as sodium N-palmitoylglutamate, N-methyl-N-acylalanine sodium, and sodium α-olefinsulfonates.

As the cationic surfactant, any of those of amine salt type and quaternary ammonium salt type can be preferably used. More specific examples include distearyldimethylbenzylammonium chloride, benzalkonium chloride, hexadecyltrimethylammonium bromide, hexadecyltrimethylammonium bromide, myristyltrimethylammonium bromide, and so forth.

Examples of the ampholytic surfactant include those of amino acid type (alkylaminofatty acid salts), betaine type (alkyl betaines), amine oxide type (alkylamine oxides), and so forth, but it is not particularly limited. More specific examples include dimethylammoniopropanesulfonates, dodecyldimethylammoniobutyrates, lauryl betaine, and amidopropyl betaine. Further specific examples include n-tetradecyl-N,N-dimethyl-3-ammonio-1-propanesulfonate, n-decyl-N,N-dimethyl-3-ammonio-1-propanesulfonate, n-dodecyl-N,N-dimethyl-3-ammonio-1-propanesulfonate, n-tetradecyl-N,N-dimethyl-3-ammonio-1-propanesulfonate, n-hexadecyl-N,N-dimethyl-3-ammonio-1-propanesulfonate, and N-dodecyl-N,N-(dimethylammonio)butyrate.

Example of Composition

In a particularly preferred embodiment, the lysis agent comprises lysozyme, labiase, and a nonionic surfactant. Such a lysis agent is effective for various *Streptococcus* bacteria, and it is especially effective for *Streptococcus uberis* or *Streptococcus agalactiae*. For the lysis agent containing lysozyme, labiase, and a nonionic surfactant, particularly preferred examples of the nonionic surfactant include a polyoxyethylene alkyl phenyl ether, and/or a polyoxyethylene sorbitan fatty acid ester, and more preferred examples include a polyoxyethylene alkyl phenyl ether and a polyoxyethylene sorbitan fatty acid ester. Concentrations of such ingredients of the lysis agent can be determined so that, in the step of lysing the bacteria existing in milk by mixing the lysis agent with the milk, the final concentration of lysozyme is not lower than 0.6 mg/ml and not higher than 50 mg/ml, the final concentration of labiase is not lower than 0.05 mg/ml and not higher than 20 mg/ml, and the final concentration of the nonionic surfactant is not lower than 0.03% and not higher than 3%. With a more preferred embodiment of the lysis agent containing lysozyme, labiase, and a nonionic surfactant, in the step of lysing bacteria existing in milk by mixing the lysis agent with the milk, the final concentration of lysozyme is not lower than 0.5 mg/ml and not higher than 50 mg/ml, the final concentration of labiase is not lower than 0.1 mg/ml and not higher than 10 mg/ml, and the final concentration of the nonionic surfactant is not lower than 0.10% and not higher than 2.6%.

[Other Ingredients]

The lysis agent of the present invention may contain, besides the lytic enzyme and the surfactant, one or more kinds of other ingredients, so long as the intended effect is not markedly degraded. Preferred examples of the ingredients other than the lytic enzyme and the surfactant include a substance that has an effect of promoting the lysis. Specific examples include glutaraldehyde, halogen compounds, chlorhexidine, alcohols (for example, methanol, ethanol, 1-propanol, 2-propanol, 1-butanol, 2-butanol, 2-methyl-1-propanol, 2-methyl-2-propanol), phenol, hydrogen peroxide, acrinol, guanidine and salt thereof, chelating agents, organic acids (e.g., decanoic acid) and salts thereof, polyhydric alcohols (for example, ethylene glycol, propylene glycol, diethylene glycol, glycerin, and monocaprylin), and reducing agents such as 2-mercaptoethanol, dithiothreitol, cystine, and thiophenol, but they are not limited to these.

For example, when either one of guanidine and a salt thereof (for example, guanidine thiocyanate) is used, as for the lower limit of the final concentration thereof at the time of mixing with milk, the concentration (when two or more kinds of the substances are used, it is the concentration as the total concentration of them) can be 0.1 mM or higher, preferably 1 mM or higher, more preferably 1 mM or higher. In any case, as for the upper limit of the final concentration at the time of mixing with milk, the concentration can be 500 mM or lower, preferably 200 mM or lower, more preferably 100 mM or lower.

Examples of the chelating agent include ethylenediaminetetraacetic acid (EDTA) and a salt thereof, glycol ether-diaminetetraacetic acid (EGTA) and a salt thereof, polyphosphoric acid and a salt thereof, as well as metaphosphoric acid and a salt thereof. As for the lower limit of the final concentration thereof at the time of mixing with milk, the concentration (when two or more kinds of the chelating agents are used, it is the concentration as the total concentration of them) can be 0.001 mM or higher, preferably 0.01 mM or higher, more preferably 0.1 mM or higher. In any case, as for the upper limit of the final concentration at the time of mixing with milk, the concentration can be 100 mM or lower, preferably 10 mM or lower, more preferably 5 mM or lower, from the viewpoint of suppressing inhibition of an antigen-antibody reaction.

[Lysis Conditions and Lysis Ratio]

In the present invention, the lysis agent can be used by mixing it with milk. Mixing ratio of milk and the lysis agent is not particularly limited, so long as the final concentrations of the lytic enzyme etc. are properly maintained, and sufficient lysis ratio can be secured. If the lysis agent is used in a volume relatively small with respect to milk, the milk is not diluted. Therefore, it can be expected that cells can be detected with higher sensitivity. When the lysis agent is used in a volume relatively large with respect to milk, influences of fat globules and proteins contained in milk are reduced, and therefore it can be expected that cells can be detected in a shorter time. From the viewpoint that a higher ratio of milk in the mixture of milk and the lysis agent (milk/(milk+lysis agent)×100) can provide higher detection sensitivity, the ratio can be, for example, 5% or higher, preferably 10% or higher, more preferably 20% or higher, further preferably 30% or higher, irrespective of the other conditions. As for the upper limit of the ratio, if the lysis agent solidified by drying or the like is used, the ratio of milk can be made to be 100%, irrespective of the other conditions. The ratio of the milk can be 90% or lower, 80% or lower, 70% or lower, 60% or lower, or 50% or lower, irrespective of the other conditions. As for the upper limit, the ratio may be determined in consideration of ease of mixing, stability of the lysis agent as a solution, and so forth.

In the present invention, it is sufficient to simply mix milk with the lysis agent. Temperature at the time of mixing, and treatment time for allowing the enzyme to act following the mixing are not particularly limited, so long as the lytic enzyme used can exhibit the activity, and the temperature may usually be room temperature. The treatment time for allowing the reaction after the mixing can be appropriately determined by those skilled in the art in consideration of lysis ratio. In the present invention, since combination and concentrations of lytic enzymes appropriate for Streptococcus bacteria are used, the treatment time can be shortened compared with that obtainable by use of a usual lysis method. In the present invention, in any case, the treatment time is generally about several tens of minutes to several hours, and more specifically, it can be 240 minutes or shorter, preferably 150 minutes or shorter, more preferably 90 minutes or shorter, still more preferably 60 minutes or shorter, further preferably 45 minutes or shorter, still further preferably 25 minutes or shorter, still more further preferably 20 minutes or shorter, particularly preferably 15 minutes or shorter. The treatment time can also be made to be substantially 0 (after milk and the lysis agent are mixed, the mixture is immediately subjected to the measurement). Temperature can be, in any case, 2 to 50° C., for example, 35 to 40° C., and it can be determined as required in consideration of type of the enzyme and treatment time to be used. The treatment can be performed in a stationary state, or with stirring. According to the present invention, even with such a short period of time, required lysis can be attained, and detection of Streptococcus bacteria can be enabled. In the present invention, a surfactant can also be used in combination with the lytic enzyme. In such a case, the treatment time may be shortened compared with the case of using only a lytic enzyme, or the lysis ratio may be increased even with the same treatment time. The treatment time is generally about several tens of minutes to several hours, and more specifically, it can be 240 minutes or shorter, preferably 150 minutes or shorter, more preferably 90 minutes or shorter, still more preferably 60 minutes or shorter, further preferably 45 minutes or shorter, still further preferably 25 minutes or shorter, still more further preferably 20 minutes or shorter, particularly preferably 15 minutes or shorter. The treatment time can also be made to be substantially 0 (after milk and the lysis agent are mixed, the mixture is immediately subjected to the measurement). Also when a surfactant is used in combination, temperature can be, in any case, 2 to 50° C., for example, 35 to 40° C., and it can be determined as required in consideration of type of the enzyme and treatment time to be used. Also in this case, the treatment can be performed in a stationary state, or with stirring.

As for the lysis ratio referred to in the present invention, lysis ratio observed for a suspension of a target Streptococcus bacterium subjected to a preliminary treatment with a nonionic surfactant of a proper concentration, then further subjected to ultrasonication, and a sufficient enzyme treatment, as required, can be defined as 100%, unless especially indicated.

[Detection Means]

Streptococcus bacteria lysed according to the present invention can be detected by various kinds of immunological methods using an ingredient of bacterial cells as an antigen. For example, an antigen consisting of the ribosomal L7/L12 protein of a Streptococcus bacterium can be detected by an immunochromatographic method, or the aforementioned antigen can also be detected by another immunological measurement method instead of the immunochromatographic method. Examples of immunological measurement method other than the immunochromatographic method include, for example, agglutination reaction method, enzyme immunoassay (ELISA), radioimmunoassay (RIA), fluoroimmunoassay (FIA), and so forth, but it is not limited to these.

At the time of performing the immunological methods, a substance for blocking for preventing non-specific adsorption, or a substance for preventing cross-reaction with bacteria other than the target bacterium may be used. In particular, in order to prevent reaction of the antibody used and the protein A of Staphylococcus aureus, globulin that does not participate in the reaction with the antigen can be added. When globulin is used, it can be added in an amount of 0.01 µg/ml or larger, preferably 0.1 µg/ml or larger, more preferably 1 µg/ml or larger, as the final concentration at the time of the reaction, from the viewpoint of suppressing false positive results. Further, in any case, from the viewpoint of not inhibiting the objective antigen-antibody reaction, it can be used in an amount of 10 mg/ml or smaller, preferably 5 mg/ml or smaller, more preferably 1 mg/ml or smaller. Such conditions concerning the final concentration are especially suitable for the immunochromatographic method.

When an immunochromatographic method is used, it can be carried out typically as follows.

[Immunochromatographic Method and Immunochromatographic Device]

An antigen-antibody reaction can be detected by the sandwich assay using a "labeled first antibody directed to a specific substance" retained by a first part, and a "second antibody directed to the specific substance" immobilized on a second part. Alternatively, an antigen-antibody reaction may also be detected by the competition method using a labeled specific substance retained by a first part, and an antibody directed to the specific substance immobilized on a second part. However, in the present invention, the sandwich assay method is preferred, since it shows high detection sensitivity and gives a line indicating detection of antibody as a positive result.

Figure 2:
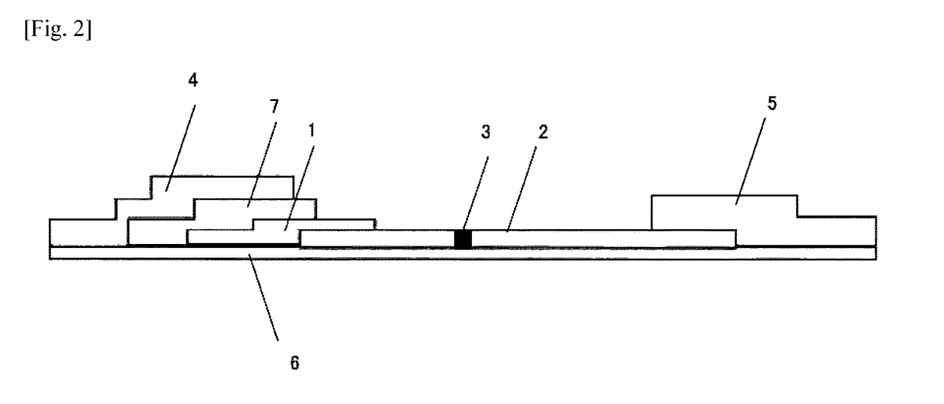
FIG. 2 shows a schematic sectional view of the test strip of the immunochromatographic device prepared in Example 3, which comprises a labeled antibody-impregnated member 1 (first part), a membrane carrier 2 for chromatographic development (second part), a part 3 for capturing, a member 4 serving as both a member for sample addition and a member for removal of fat globules (third part), a member 5 for absorption, a substrate 6, and a member 7 for removal of fat globules (third part).

The immunochromatographic device is a device for detecting a specific substance contained in milk by an immunochromatographic method, which comprises a test strip having a first part retaining a labeled first antibody directed to the specific substance, or the specific substance that is labeled, a second part disposed downstream from the first part, on which a second antibody directed to the specific substance is immobilized, and a third part disposed upstream from the first part or the second part and having voids enabling removal of milk fat globules contained in the milk. As a specific example of the structure of the test strip, that of the test strip of which schematic sectional view is shown in FIG. 2 can be mentioned. In FIG. 2, a member 7 for removal of fat globules (third part) is disposed downstream from a member 4 for sample addition, and upstream from a labeled antibody-impregnated member (first part) 1.

The immunochromatographic device can be produced in a known manner by using marketed materials.

The material used for the first part is not particularly limited, so long as a material enabling immunochromatography is chosen, but preferred examples include a fiber matrix of cellulose derivative etc., filter paper, glass fiber, cloth, cotton, and so forth.

The material used for the second part is not particularly limited, so long as a material enabling immunochromatography is chosen, but preferred examples include cellulose nitrate, mixed cellulose nitrate ester, polyvinylidene fluoride, nylon, and so forth.

The material used for the third part preferably has voids that enable removal of milk fat globules contained in milk and having a diameter of about 1 to ten and several micrometers. The third part must be disposed upstream from the aforementioned second part consisting of a porous membrane having a pore diameter of several tens to several hundreds nm, and is preferably disposed upstream from the aforementioned first part, i.e., at a position at which a sample solution first contacts with and passes through the test strip.

The voids of the third part may have a size that enables removal of milk fat globules, and retention particle size is preferably 0.1 to 10 μm, more preferably 1 to 3.5 μm. The material is not particularly limited, so long as a material having voids showing a retention particle size within the aforementioned range is chosen, but preferred examples include a matrix of fibers such as cellulose derivatives, filter paper, glass fiber, cloth, cotton, and so forth. The retention particle size means such a particle size of milk fat globules that milk fat globules having a particle size not smaller than the retention particle size cannot pass through the voids and retained by the third part, and substantially corresponds to average pore size of the voids of the third part, and 50% or more, preferably 60% or more, more preferably 70% or more, still more preferably 80% or more, particularly preferably 90% or more, most preferably 98% or more, of milk fat globules having a particle size not smaller than the retention particle size cannot pass through the voids and are retained by the third part. Ratio of milk fat globules to be retained can be measured by a method well known to those skilled in the art. For example, the catalogue of GF/B provided by GE Healthcare Bioscience describes that the retention particle size (particle diameter for which retention efficiency is 98%, the term retention particle size used in this specification has this meaning, unless especially indicated) thereof is 1.0 μm, and such a particle size as mentioned above can be confirmed by a method well known to those skilled in the art.

The aforementioned third part may consist of a single kind of material having a specific retention particle size, or may consist of a laminate comprising materials having different retention particle sizes and integrally adhered so that the retention particle size becomes smaller stepwise, in order to increase milk fat globule separation efficiency. Such a third part as mentioned above constituted by two or more kinds of members that can remove milk fat globules of different particle sizes constitutes a preferred embodiment of the present invention, and in a more preferred embodiment of the present invention, the third part is constituted with a first member disposed downstream and a second member disposed upstream, and the retention particle size of the second member is larger than the retention particle size of the first member. When the third part is constituted with such two kinds of members, it is preferred that the retention particle size of the first member disposed downstream is 1.0 to 2.0 μm, and the retention particle size of the second member disposed upstream is 3.0 to 3.5 μm. In order to highly sensitively detect a specific substance from milk containing milk fat globules of high concentration and wide particle size distribution, especially such milk not diluted after milking, it is preferred that the third part is constituted with a combination of a member having a small retention particle size and a member having a large retention particle size.

The aforementioned first part retains a labeled first antibody directed to a specific substance, or a labeled specific substance. If the first part retains a labeled first antibody directed to a specific substance, the specific substance can be detected by the sandwich assay method. If the first part retains a labeled specific substance, the specific substance can be detected by the competition method. Since the sandwich assay method that shows high detection sensitivity and gives a line indicating detection of antibody as a positive result is more preferred for the present invention, the first part preferably retains a labeled first antibody directed to a specific substance.

When the first part is made to retain a labeled first antibody directed to a specific substance, two kinds of antibodies, the first antibody directed to the specific substance, and a second antibody also directed to the specific substance, are used. In order to enable detection of the specific substance by the sandwich assay method, the aforementioned first antibody and second antibody are antibodies that can simultaneously bind to the specific substance, and it is preferred that the epitope of the specific substance to be recognized by the aforementioned first antibody is different from the epitope of the specific substance to be recognized by the aforementioned second antibody.

In the present invention, in order to obtain a detectable signal, the first antibody or the specific substance retained by the first part is labeled. Examples of the label used for the present invention include a colored particle, enzyme, radioisotope, and so forth, and it is preferable to use a colored particle that can be visually detected without any special equipment. Examples of the colored particle include metal microparticles such as those of gold and platinum, nonmetallic particles, latex particles, and so forth, but are not limited to these. The colored particle may have any size so long as the colored particle has such a size that it can be transported downstream through the inside of the voids of the test strip, but it preferably has a size of 1 nm to 10 more preferably 5 nm to 1 μm, still more preferably 10 to 100 nm, in diameter.

[Object of Detection]

According to the present invention, a *Streptococcus* bacterium contained in milk can be detected. The "*Streptococcus* bacterium" referred to in the present invention may be *Streptococcus uberis, Streptococcus agalactiae, Streptococcus dysgalactiae, Streptococcus equinus, Streptococcus canis, Streptococcus bovis, Streptococcus pluranimalium, Streptocoloccus parauberis, Streptococcus mutans, Streptococcus acidominimus*, or the like, unless especially indicated. According to the present invention, *Streptococcus* bacteria contained in milk obtained from a livestock animal such as cow as it is, which contains fat globules and proteins of high concentration, can be detected by using the lysis agent containing appropriately formulated lytic enzyme and surfactant.

The specific substance measured in the present invention may be any substance so long as it is a substance that can be measured by an immunological method such as immunochromatographic method, but it is preferably a component of a bacterium or a substance that is secreted by a bacterium. The specific substance is more preferably the L7/L12 ribosomal protein of a bacterium. High detection sensitivity can be obtained for the L7/L12 ribosomal protein, since it exists in cells in a large copy number.

[Antibody]

The antibody used in the present invention can be prepared by the method described in International Patent Publication WO00/06603. When the bacterial ribosomal protein L7/L12 is used as the antigen, the antibody can be prepared by using a full length protein or a partial peptide of the bacterial ribosomal protein L7/L12 as an antigen, but it is preferably prepared by using the full length protein as an antigen. An antiserum containing an antibody (polyclonal antibody) that recognizes the L7/L12 ribosomal protein can be obtained by inoculating such a partial peptide or full length protein as mentioned above as it is or crosslinked with a carrier protein to an animal, together with an adjuvant as required, and collecting the serum of the animal. Further, the antibody purified from the antiserum can also be used. Examples of the animal used for the inoculation include sheep, horse, goat, rabbit, mouse, rat, and so forth, and sheep, rabbit, and so forth are especially preferred for preparing polyclonal antibodies. Further, it is more preferable to use, as the antibody, a monoclonal antibody obtained by a known method in which a hybridoma cell is prepared, and in such a case, mouse is preferred as the animal. If, as such a monoclonal antibody, a monoclonal antibody that reacts with the ribosomal protein L7/L12 of a specific bacterium that causes mastitis, but does not react with the ribosomal protein L7/L12 of a bacterium that causes mastitis other than the above specific bacterium is retrieved by screening, it can be utilized for diagnosing whether an animal suffers from infection by the bacterium or not.

A monoclonal antibody that recognizes a substance other than the ribosomal protein L7/L12 as an antigen may also be used, so long as the antibody is a monoclonal antibody that reacts with a component of a specific bacterium that causes mastitis or a substance secreted by such a bacterium, but does not react with a component of a bacterium that causes mastitis other than the foregoing specific bacterium or a substance secreted by such a bacterium.

Further, as the monoclonal antibody, it is preferable to use a monoclonal antibody of which antigen-antibody reaction is not inhibited by any contaminants other than the specific substance contained in milk. For example, milk contains a large amount of proteins such as casein, and they may inhibit the reaction of the specific substance and the monoclonal antibody. When a monoclonal antibody directed to the specific substance is prepared in a conventional manner, for example, a monoclonal antibody of which antigen-antibody reaction is not inhibited by casein or the like, or a monoclonal antibody of which antigen-antibody reaction is hardly affected by casein or the like may be preferably chosen and used. Such a monoclonal antibody can be easily obtained by preparing monoclonal antibodies that specifically react with an antigen in a usual manner, and then selecting a monoclonal antibody of which antigen-antibody reaction is not substantially inhibited by a contaminant such as casein by examining whether the antigen-antibody reaction is inhibited or not in the presence of the contaminant.

EXAMPLES

Example 1

(1) Preparation of Ribosomal Protein L7/L12 Antibody

According to the method described in the examples of International Patent Publication WO00/06603, the L7/L12 ribosomal protein was obtained, and monoclonal antibodies were prepared by using this protein. Among the monoclonal antibodies, a combination of two kinds of monoclonal antibodies that can simultaneously bind to different sites of the aforementioned L7/L12 ribosomal protein was selected.

(2) Evaluation of Lytic Activity by ELISA

*S. uberis* or *S. agalactiae* cell count was adjusted to $1 \times 10^9$ (cells/ml) with physiological saline to prepare a cell suspension. Further, 6 kinds of the enzymes shown in Table 1 were each diluted with a 1:1 (v/v) mixture of milk and each buffer to a concentration of 1 mg/ml or 10 mg/ml to prepare enzyme solutions.

TABLE 1

| Lytic enzyme | Manufacturer | Buffer | Concentration of enzyme solution (final concentration after mixing with cell suspension) |
|---|---|---|---|
| Labiase (Lot, BDBAC12)*1 | Ozeki | Citrate/phosphate Na, pH 4 | 1 mg/ml (0.5 mg/ml) |

TABLE 1-continued

| Lytic enzyme | Manufacturer | Buffer | Concentration of enzyme solution (final concentration after mixing with cell suspension) |
|---|---|---|---|
| Lysozyme *2 | Wako Pure Chemical Industries | Citrate/phosphate Na, pH 4 | 10 mg/ml (5 mg/ml) |
| Lysostaphin | Wako Pure Chemical Industries | Tris-HCl, pH 8 | 10 mg/ml (5 mg/ml) |
| Achromopeptidase | Wako Pure Chemical Industries | Tris-HCl, pH 8 | 10 mg/ml (5 mg/ml) |
| β-N-Acetyl-glucosaminidase *3 | Sigma-Aldrich | Citrate/phosphate Na, pH 4 | 10 mg/ml (5 mg/ml) |
| Proteinase K | Sigma-Aldrich | Tris-HCl, pH 8 | 0.1 mg/ml (0.05 mg/ml) |

*1β-N-Acetyl-D-glucosaminidase activity, 19.13 U/g-powder; Protein, 24.00 mg-protein/g-powder; Lysis of lactic acid bacterium cells with 0.5% (w/v) labiase
*2: Titer, 0.8 mg lysozyme/mg or higher (Wako Pure Chemical Industries Product Standard)
*3: >80 units/mg protein As a positive control, a disrupted cell suspension obtained by stirring S. uberis or S. agalactiae cells overnight in the MOPSO buffer (0.1 M) containing 1% nonionic surfactant Triton X-100, and then ultrasonicating the cell suspension (output 10%, 1 minute×10 times) was used.

The monoclonal antibody 1 (10 µg/ml) in 0.05% $NaN_3$/PBS (50 µl) was put into each well of a 96-well ELISA plate (Maxsorp ELISA Plate, Nunc), and adsorption of the antibody was allowed overnight at 4° C. After the supernatant was removed, a 1% bovine serum albumin solution (in PBS, 200 µl) was added, and the reaction was allowed at room temperature for 1 hour to attain blocking. After the supernatant was removed, each well was washed several times with a washing solution (0.05% Tween 20, PBS).

The bacterial cell suspension and the enzyme solution prepared above were mixed at a volume ratio of 1:1, treated for 1 hour in an incubator at 37° C., and diluted 100 times with 0.05% Tween 20 in PBS, the diluted suspension (50 µl) was added to each well of the plate, and the reaction was allowed at 37° C. for 1 hour. After the supernatant was removed, wells were washed several times with the washing solution, 50 µl of the monoclonal antibody-2 (1 µg/ml, 0.05% Tween 20 in PBS) labeled with peroxidase was added, and the reaction was allowed at room temperature for 1 hour. After the supernatant was removed, wells were further washed several times with the washing solution, then a TMB solution (100 µl, KPL) was added to each well, and the reaction was allowed at room temperature for 10 minutes. Then, 1 mol/1 hydrochloric acid (100 µl) was added to terminate the reaction, and absorbance was measured at 450 nm.

Lysis ratio was calculated for each enzyme from a ratio of the absorbance to that of the positive control, of which lysis ratio was taken as 100%. A lysis ratio of 5% or higher is indicated with +, and that lower than 5% is indicated with −. The results are shown in Table 2.

TABLE 2

| Lytic enzyme | S. uberis | S. agalactiae |
|---|---|---|
| Lysozyme | + | + |
| Labiase | + | + |
| Lysostaphin | − | − |
| Achromopeptidase | − | − |
| β-N-Acetylglucosaminidase | − | + |
| Proteinase K | − | − |

Each of lysozyme and labiase brought about the effect by itself on both the bacteria. β-N-Acetylglucosaminidase brought about the effect by itself on S. agalactiae.

Example 2

Figure 1:
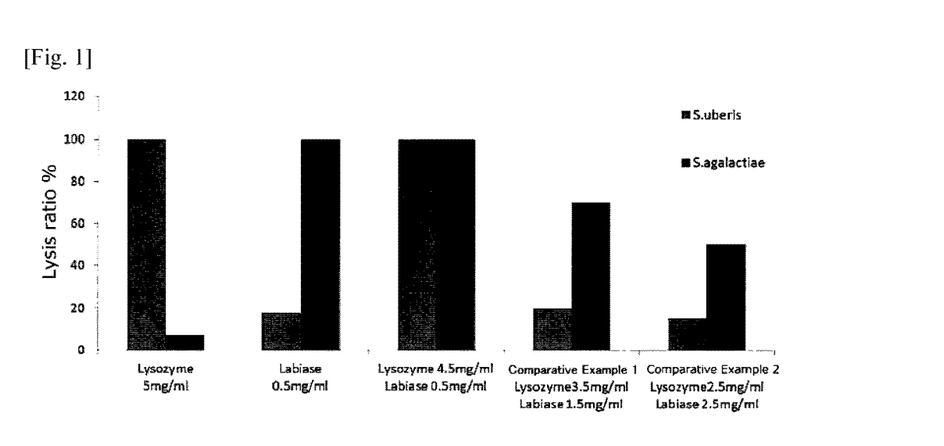
FIG. 1 shows effect of a lytic enzyme in detection of a *Streptococcus* bacterium by enzyme immunoassay (ELISA).

The bacteria were treated in the same manner as described above with labiase and lysozyme at final concentrations of 0.5 mg/ml and 4.5 mg/ml, respectively, adjusted with a mixture of a citrate-phosphate Na buffer and milk (mixing ratio in volume was 1:1). The results for lysis ratio calculated from the results of ELISA are shown in FIG. 1. It was revealed that when lysozyme or labiase was used alone, the bacteriolytic activity was insufficient for either the bacterium S. uberis or S. agalactiae, but if they are used in combination as a mixture in certain concentration ranges thereof, both the bacteria can be highly efficiently lysed.

Example 3: Preparation of Immunochromatographic Device

An immunochromatographic device was prepared as follows.

(a) Gold Colloid-Labeled Antibody-Impregnated Member

A gold colloid solution (particle size 60 nm, 0.9 mL, BB International) was mixed with 0.1 M potassium phosphate, pH 7.0, a monoclonal antibody 1 (100 µg/mL) to be labeled with gold colloid was added to the mixture, and the resulting mixture was left standing at room temperature for 10 minutes so that the antibody bound to the gold colloid particle surfaces. Then, a 10% aqueous solution of bovine serum albumin (BSA) was added at a final concentration of 1% in the gold colloid solution, so that the remaining surfaces of the gold colloid particles were blocked with BSA, to prepare a solution of the monoclonal antibody 1 labeled with gold colloid (henceforth referred to as "gold colloid-labeled antibody"). This solution was centrifuged (at 15000 rpm for 5 minutes) to precipitate the gold colloid-labeled antibody, and the supernatant was removed to obtain the gold colloid-labeled antibody. This gold colloid-labeled antibody was suspended in 20 mM Tris-hydrochloric acid buffer (pH 7) containing 0.25% BSA, 2.5% sucrose, and 35 mM NaCl to obtain a gold colloid-labeled antibody solution. A glass fiber pad of a strip-like shape (10 mm×300 mm) was impregnated with the gold colloid-labeled antibody solution (2 mL), and dried at room temperature under reduced pressure to obtain a gold colloid-labeled antibody-impregnated member 1 (first part).

(b) Part for Capturing Complex of Antigen and Gold Colloid-Labeled Antibody

A nitrocellulose membrane having a width of 25 mm and a length of 300 mm was prepared as a membrane carrier 2 for chromatographic development with chromatography medium (second part).

A solution containing the monoclonal antibody 2 (1.5 mg/mL) was applied in the shape of a line in a volume of 1 µL/cm to the membrane carrier 2 for chromatographic development at a position of 10 mm from the end on the side of the chromatography development starting point, and dried at 50° C. for 30 minutes, and then the membrane carrier was immersed in a 0.5% sucrose solution for 30 minutes, and dried overnight at room temperature to obtain a part 3 for capturing the complex of the ribosomal protein L7/L12 antigen and the gold colloid-labeled antibody.

(c) Preparation of Immunochromatographic Device

A sectional view of immunochromatographic device is shown in FIG. 2. In addition to the aforementioned labeled antibody-impregnated member 1 and membrane carrier 2 for chromatographic development, 25 mm GF/DVA (filter member 4 having a thickness of 776 µm and consisting of glass fibers, retention particle size 3.5 µm, GE Healthcare Bioscience) and 20 mm GF/AVA (filter member 7 having a thickness of 299 µm and consisting of glass fibers, retention particle size 1.7 µm, GE Healthcare Bioscience) were adhered to each other as a member serving as both the member for sample addition and the member for removal of fat globules (third part), and filter paper as the member 5 for absorption was further prepared. After these members were adhered on a substrate 6 (thickness 254 µm, made of polystyrene, having adhesive for adhering the members), they were cut in a width of 5 mm to prepare the immunochromatographic device.

Example 4: Evaluation of Bacteriolytic Activity by Immunochromatography 1

Measurement for cow's milk using the immunochromatographic device was performed as follows. Milk (300 µl) containing *Streptococcus uberis* at a final concentration of $1 \times 10^5$ (CFU/ml) was put into a microtube, 500 µl of a lysis treatment solution was added to the milk, and the treatment was performed at room temperature for 30 minutes. As the cow's milk, marketed milk for drinking was used. The aforementioned immunochromatographic device was immersed into the above mixed solution from the member 4 for sample addition, chromatographic development was allowed by leaving the device standing at room temperature for 30 minutes, and then for determining the presence or absence of capture of the complex of the ribosomal protein L7/L12 antigen and the gold colloid-labeled antibody by the aforementioned part 3 for capturing, intensity of a reddish purple line that became more or less conspicuous in proportion to the capture amount was measured. The lysis ratios observed under various conditions are shown in Table 3.

TABLE 3

|  | Condition 1 | Condition 2 | Condition 3 | Comparative Example 3 |
|---|---|---|---|---|
| Enzyme 1 | 0.25 mg/ml Labiase | 0.25 mg/ml Labiase | 0.25 mg/ml Labiase | 5 mg/ml Lysozyme |
| Enzyme 2 | None | 0.75 mg/ml Lysozyme | 0.75 mg/ml Lysozyme | 4 mg/ml Achromopeptidase |
| Surfactant 1 (final concentration, wt/wt %) | 0.6% Triton X-100 | 0.6% Triton X-100 | 0.6% Triton X-100 | 0.2% Sodium N-lauroyl salcosinate |
| Surfactant 2 (final concentration, wt/wt %) | None | None | 0.6% Tween 20 | 0.2% Brij 58 |
| Lysis ratio for *S. uberis* | 35.0 | 48.0 | 56.1 | 1.5 |

It was revealed that, compared with the condition 1, in which only labiase was used, the lysis ratio was improved with the condition 2, in which lysozyme was used in combination, and the condition 3, in which Tween 20 (polyoxyethylene sorbitan fatty acid ester) was further added as a surfactant. Further, when the condition described in Non-patent document 1 (Comparative Example 3) was retested, a low lysis ratio was observed.

Example 5: Evaluation of Bacteriolytic Activity by Immunochromatography 2

Addition amount of lysozyme used in combination with labiase was evaluated by using the same method as that used in Example 4. The results are shown in Table 4. It was confirmed that addition of appropriate amount of lysozyme improves lysis ratio.

TABLE 4

|  | Condition 3 | Condition 4 | Condition 5 | Comparative Example 9 |
|---|---|---|---|---|
| Enzyme 1 | 0.25 mg/ml Labiase | | | |
| Enzyme 2 | Lysozyme 0.75 mg/ml | Lysozyme 1.25 mg/ml | Lysozyme 3 mg/ml | Lysozyme 6.25 mg/ml |
| Surfactant 1 (final concentration, wt/wt %) | 1% Triton X-100 | | | |
| Surfactant 2 (final concentration, wt/wt %) | 1.3% Tween 20 | | | |
| Lysis ratio for *S. uberis* | 56.1 | 62.2 | 67.3 | 15 (bad flow of test liquid) |

Example 6: Evaluation of Surfactant Concentration by Immunochromatography

Concentration of surfactants was evaluated by using the same method as that used in Example 4. The results are shown in Table 5. It was revealed that if the addition amounts of Triton X-100 and Tween 20 are appropriate, the lysis ratio is further improved.

TABLE 5

|  | Condition 3 | Condition 6 | Condition 7 | Condition 8 | Condition 9 | Condition 10 | Comparative Example 7 | Comparative Example 8 |
|---|---|---|---|---|---|---|---|---|
| Enzyme 1 | 0.25 mg/ml Labiase | 0.25 mg/ml Labiase | 0.25 mg/ml Labiase | 0.25 mg/ml Labiase | 0.25 mg/ml Labiase | 0.25 mg/ml Labiase | 0.25 mg/ml Labiase | 0.25 mg/ml Labiase |
| Enzyme 2 | 0.75 mg/ml Lysozyme | 0.75 mg/ml Lysozyme | 0.75 mg/ml Lysozyme | 0.75 mg/ml Lysozyme | 0.75 mg/ml Lysozyme | 0.75 mg/ml Lysozyme | 0.75 mg/ml Lysozyme | 0.75 mg/ml Lysozyme |
| Surfactant 1 (final concentration, wt/wt %) |  | 0.6% Triton X-100 |  | 1% Triton X-100 |  | 1.3% Triton X-100 | 1% Triton X-100 | 2.5% Triton X-100 |
| Surfactant 2 (final concentration, wt/wt %) | 0.6% Tween 20 | 1% Tween 20 | 1.3% Tween 20 | 1% Tween 20 | 1.3% Tween 20 | 1.3% Tween 20 | 2.5% Tween 20 | 2.5% Tween 20 |
| Lysis ratio of S. uberis | 56.1 | 70.4 | 69.8 | 60.9 | 62.6 | 83.5 | 44.6 | 38.4 |

Example 7: Detection Sensitivity for Live Cells Contained in Milk

Samples prepared by adding *Streptococcus uberis* at various concentrations to milk were treated with the lysis agents of the conditions 1 and 10, and measurement was carried out by immunochromatography. A reddish purple line appeared was visually examined (strongly positive ++, positive +, negative −).

TABLE 6

| Number of bacteria CFU/mL | Condition 1 | Condition 10 |
|---|---|---|
| $1 \times 10^4$ | − | + |
| $2 \times 10^4$ | − | + |
| $5 \times 10^4$ | + | + |
| $1 \times 10^5$ | + | ++ |

Example 8: Improvement of Lysis Ratio with Additives

Lysis ratios obtainable with the lysis agents of the condition 9 mentioned in Example 6 and further containing various additives were evaluated. The results are shown in Table 7.

TABLE 7

|  | Condition 9 | Condition 11 | Condition 12 | Condition 13 | Condition 14 | Condition 15 | Condition 16 |
|---|---|---|---|---|---|---|---|
| Enzyme | 0.25 mg/ml Labiase, 0.75 mg/ml Lysozyme | | | | | | |
| Surfactant | 1% Triton X-100, 1.3% Tween 20 | | | | | | |
| Additive | None | 50 mM NaCl | 50 mM Guanidine thiocyanate | 10 mM Decanoic acid | 0.1 mM Monocaprylin | 1 mM EDTA | 1 mM EGTA |
| Lysis ratio | 62.6% | 71.7% | 85.4% | 89.2% | 91.2% | 91.1% | 92.4% |

* Monocaprylin: 1-monooctanoylglycerol, Tokyo Chemical Industry

INDUSTRIAL APPLICABILITY

The present invention can be utilized for quick diagnosis of mastitis of livestock animals based on the immunochromatographic method, or the like.

The invention claimed is:

1. A method for lysing a *Streptococcus* bacterium contained in milk, which comprises
   the step of mixing a lysis agent containing lysozyme, labiase, and a nonionic surfactant with the milk to lyse the bacterium existing in the milk,
   wherein, in the step of mixing the lysis agent with the milk to lyse the bacterium existing in the milk, final concentration of the nonionic surfactant is not higher than 3%.

2. The lysis method according to claim 1, wherein the bacterium is *Streptococcus uberis* or *Streptococcus agalactiae*.

3. The lysis method according to claim 1, wherein the nonionic surfactant comprises a polyoxyethylene alkyl phenyl ether and/or a polyoxyethylene sorbitan fatty acid ester.

4. The lysis method according to claim 1, wherein, in the step of mixing the lysis agent with the milk to lyse the bacterium existing in the milk, final concentration of the nonionic surfactant is not lower than 0.03% and not higher than 3%.

5. The lysis method according to claim 4, wherein, in the step of mixing the lysis agent with the milk to lyse the bacterium existing in the milk, final concentration of lysozyme is not lower than 0.5 mg/ml and not higher than 200 mg/ml; and/or in the step of mixing the lysis agent with the milk to lyse the bacterium existing in the milk, final concentration of labiase is not lower than 0.05 mg/ml and not higher than 20 mg/ml.

* * * * *